United States Patent [19]

Davey et al.

[11] Patent Number: 6,080,745
[45] Date of Patent: Jun. 27, 2000

[54] FUSED TRICYCLIC HETEROAROMATIC DERIVATIVES AS DOPAMINE RECEPTOR SUBTYPE LIGANDS

[75] Inventors: William Barnaby Davey, Bishops Stortford; Paul David Leeson, Cambridge; Michael Rowley, Harlow, all of United Kingdom

[73] Assignee: Merck Sharp & Dohme Limited, Hoddesdon, United Kingdom

[21] Appl. No.: 08/617,895

[22] PCT Filed: Sep. 6, 1994

[86] PCT No.: PCT/GB94/01936

§ 371 Date: Mar. 12, 1996

§ 102(e) Date: Mar. 12, 1996

[87] PCT Pub. No.: WO95/07893

PCT Pub. Date: Mar. 23, 1995

[30] Foreign Application Priority Data

Sep. 15, 1993 [GB] United Kingdom .................... 9319110
Sep. 16, 1993 [GB] United Kingdom .................... 9319151

[51] Int. Cl.[7] ........................ A61K 31/42; A61K 31/415; C07D 231/54; C07D 261/20
[52] U.S. Cl. .......................... 514/254; 544/249; 544/250; 544/368; 544/371
[58] Field of Search ..................................... 544/371, 368, 544/249, 295, 250; 514/254

[56] References Cited

U.S. PATENT DOCUMENTS 4,946,844  8/1990  Tomari et al. .......................... 514/254
5,004,745  4/1991  Antoine et al. ........................ 514/254

FOREIGN PATENT DOCUMENTS 384 228   8/1990   European Pat. Off. .
402 644   12/1990  European Pat. Off. .
494 817   7/1992   European Pat. Off. .
94 10162  5/1994   WIPO .

OTHER PUBLICATIONS

Jones, J. H. et al. "Synthesis of 4–Substituted 2H–Naphth [1,2–b]–1,4–oxazines, a New Class of Dopamine Agonists" J. Med. Chem. 1984, 27, pp. 1607–1613.

*Primary Examiner*—Matthew V. Grumbling
*Attorney, Agent, or Firm*—Robert J. North; Melvin Winokur

[57] ABSTRACT

A class of fused tricyclic heteroaromatic compounds of formula (I) as defined in claim 1 or a salt thereof or a prodrug thereof, containing a fused pyrazole, oxazole or pyrimidine ring are ligands for dopamine receptor subtypes within the body and are therefore of use in the treatment and/or prevention of disorders of the dopamine system, such as schizophrenia.

15 Claims, No Drawings

FUSED TRICYCLIC HETEROAROMATIC DERIVATIVES AS DOPAMINE RECEPTOR SUBTYPE LIGANDS

This application is a 371 of PCT/GB94/01936, filed Sep. 6, 1994.

This invention relates to a particular class of fused tricyclic heteroaromatic compounds based on a substituted isoxazole or pyrazole moiety. These compounds are ligands for dopamine receptor subtypes within the body and are therefore of use in the treatment and/or prevention of disorders of the dopamine system, including schizophrenia, depression, nausea, Parkinson's disease, tardive dyskinesias and extrapyramidal side-effects associated with treatment by conventional neuroleptic agents, neuroleptic malignant syndrome, and disorders of hypothalamic-pituitary function such as hyperprolactinaemia and amenorrhoea.

Upper gastrointestinal tract motility is believed to be under the control of the dopamine system. The compounds according to the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of the present invention may be beneficial in controlling vascular blood flow.

The localisation of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention may therefore be of assistance in the prevention and/or treatment of such conditions as hypertension and congestive heart failure.

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., *Nature* (London), 1991, 350, 610) and $D_5$ (Sunahara et al., *Nature* (London), 1991, 350, 614) receptor subtypes have been described.

The compounds in accordance with the present invention, being ligands for dopamine receptor subtypes within the body, are accordingly of use in the treatment and/or prevention of disorders of the dopamine system.

The present invention accordingly provides a compound of formula I, or a salt thereof or a prodrug thereof:

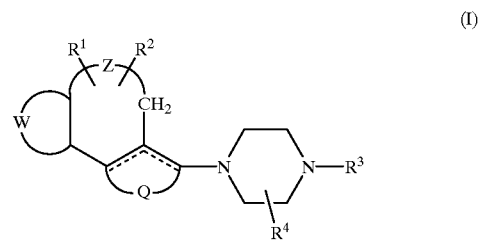

wherein the broken line represents a double bond whereby the heteroaromatic ring containing Q is aromatic;

W represents the residue of an optionally substituted aromatic or heteroaromatic ring;

Q represents the residue of a heteroaromatic ring selected from =N—NR$^5$—, —NR$^5$—N=, =N—O—, —O—N= and =N—CR$^6$=N—;

Z represents a chemical bond, an oxygen or sulphur atom, or a methylene or ethylene group;

R$^1$, R$^2$ and R$^5$ independently represent hydrogen or C$_{1-6}$ alkyl;

one of R$^3$ and R$^4$ represents hydrocarbon or a heterocyclic group, and the other of R$^3$ and R$^4$ represents hydrogen, hydrocarbon or a heterocyclic group; and R$^6$ represents C$_{1-6}$alkyl or —NR$^a$R$^b$, in which R$^a$ and R$^b$ independently represent hydrogen or C$_{1-6}$alkyl.

The compounds of the present invention are preferably prepared and utilised in the form of the free base or as a pharmaceutically acceptable salt thereof.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

For the avoidance of doubt, it will be appreciated that the present invention relates to compounds of formula (IA), and salts and prodrugs thereof:

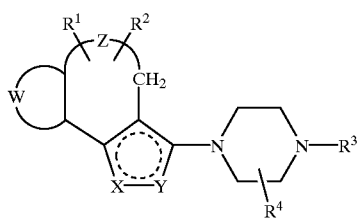

(IA)

wherein the broken circle represents two non-adjacent double bonds whereby the five-membered ring containing X and Y is aromatic;

W represents the residue of an optionally substituted aromatic or heteroaromatic ring;

one of X and Y represents nitrogen, and the other of X and Y represents oxygen or N—$R^5$;

Z represents a chemical bond, an oxygen or sulphur atom, or a methylene or ethylene group;

$R^1$, $R^2$ and $R^5$ independently represent hydrogen or $C_{1-6}$ alkyl; and one of $R^3$ and $R^4$ represents hydrocarbon or a heterocyclic group, and the other of $R^3$ and $R^4$ represents hydrogen, hydrocarbon or a heterocyclic group.

The present invention also relates to compounds of formula (IB), and salts and prodrugs thereof:

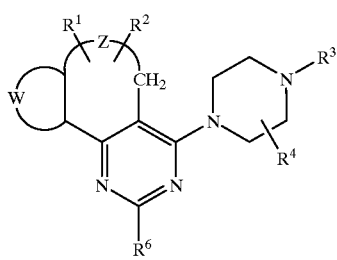

(IB)

wherein

W represents the residue of an optionally substituted aromatic or heteroaromatic ring;

Z represents a chemical bond, an oxygen or sulphur atom, or a methylene or ethylene group;

$R^1$ and $R^2$ independently represent hydrogen or $C_{1-6}$ alkyl;

one of $R^3$ and $R^4$ represents hydrocarbon or a heterocyclic group, and the other of $R^3$ and $R^4$ represents hydrogen, hydrocarbon or a heterocyclic group; and $R^6$ represents $C_{1-6}$ alkyl or —$NR^aR^b$, in which $R^a$ and $R^b$ independently represent hydrogen or $C_{1-6}$ alkyl.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, isopropyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular aryl groups include phenyl and naphthyl.

Particular aryl($C_{1-6}$)alkyl groups include benzyl, naphthylmethyl, phenethyl and phenylpropyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, indolyl, aza-indolyl, imidazolyl, oxadiazolyl and thiadiazolyl groups.

Particular heteroaryl($C_{1-6}$)alkyl groups include pyridylmethyl, pyrazinylmethyl, indolylmethyl and aza-indolylmethyl.

The hydrocarbon and heterocyclic groups may in turn be optionally substituted by one or more groups selected from $C_{1-6}$ alkyl, adamantyl, phenyl, aryl($C_{1-6}$)alkyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, trifluoromethane-sulphonyloxy, —$NR^vR^w$, —$NR^vCOR^w$, —$NR^vCO_2R^w$, —$NR^vSO_2R^w$, —$CH_2NR^vSO_2R^w$, —$NHCONR^vR^w$, —$PO(OR^v)(OR^w)$, —$CONR^vR^w$, —$SO_2NR^vR^w$ and —$CH_2SO_2NR^vR^w$, in which $R^v$ and $R^w$ independently represent hydrogen, $C_{1-6}$ alkyl, aryl or aryl($C_{1-6}$)alkyl.

The term "halogen" as used herein includes fluorine, chlorine, bromine and iodine, especially chlorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

The aromatic or heteroaromatic ring of which W is the residue is suitably a phenyl, naphthyl, furyl, thienyl, pyrrolyl or pyridyl ring, optionally substituted by one or more, preferably up to three, substituents. Examples of optional substituents on the aromatic or heteroaromatic ring of which W is the residue include halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl.

Suitably, the aromatic or heteroaromatic ring of which W is the residue is unsubstituted. Where the ring is substituted, particular substituents include methyl, ethyl, isopropyl, methoxy, benzyloxy, fluoro and chloro.

Suitably, the substituents $R^1$ and $R^2$ independently represent hydrogen or methyl, especially hydrogen.

Suitable values for the substituents $R^3$ and $R^4$ include $C_{2-6}$ alkenyl, $C_{3-7}$ cycloalkyl($C_{1-6}$)alkyl, aryl($C_{1-6}$)alkyl and heteroaryl($C_{1-6}$)alkyl, any of which groups may be optionally substituted. In addition, one of $R^3$ and/or $R^4$ may represent hydrogen. Examples of suitable substituents on the groups $R^3$ and/or $R^4$ include $C_{1-6}$ alkyl, halogen, $C_{1-6}$ alkoxy and nitro.

Particular values of $R^3$ and $R^4$ include hydrogen, allyl, cyclopropylmethyl, cyclohexylmethyl, benzyl, methyl-benzyl, chlorobenzyl, dichlorobenzyl, methoxy-benzyl, nitro-benzyl, naphthylmethyl, phenethyl, phenylpropyl and aza-indolylmethyl, provided that at least one of $R^3$ and $R^4$ is other than hydrogen. Suitably, one of $R^3$ and $R^4$ represents hydrogen, and the other of $R^3$ and $R^4$ is other than hydrogen. Preferably, $R^4$ represents hydrogen and $R^3$ is other than hydrogen.

Suitably, $R^5$ is hydrogen or methyl.

Suitable values for the substituent $R^6$ include $C_{1-6}$ alkyl, amino, $C_{1-6}$ alkylamino and di($C_{1-6}$)alkylamino. A particular value of $R^6$ is amino.

A particular sub-class of compounds according to the invention is represented by the compounds of formula IIA, and salts and prodrugs thereof:

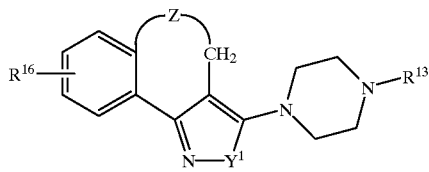

(IIA)

wherein

Z is as defined with reference to formula I above;

$Y^1$ represents oxygen or N—$R^{15}$;

$R^{13}$ represents $C_{2-6}$ alkenyl, $C_{3-7}$ cycloalkyl($C_{1-6}$)alkyl, aryl($C_{1-6}$)alkyl or heteroaryl($C_{1-6}$)alkyl, any of which groups may be optionally substituted;

$R^{15}$ represents hydrogen or $C_{1-6}$ alkyl; and $R^{16}$ represents hydrogen, halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl.

Examples of suitable substituents on the group $R^{13}$ include one or more of $C_{1-6}$ alkyl, halogen, $C_{1-6}$ alkoxy and nitro.

Particular values of $R^{13}$ with reference to formula IIA above include allyl, cyclopropylmethyl, cyclohexylmethyl, benzyl, methyl-benzyl, chlorobenzyl, dichlorobenzyl, methoxy-benzyl, nitro-benzyl, naphthylmethyl, phenethyl, phenylpropyl and aza-indolylmethyl.

Particular values of $Y^1$ with reference to formula IIA above include oxygen, NH and N-methyl.

Suitably, $R^{15}$ is hydrogen or methyl.

Particular values of $R^{16}$ include hydrogen, methyl, ethyl, isopropyl, methoxy, benzyloxy, fluoro and chloro, especially hydrogen.

Another sub-class of compounds according to the invention is represented by the compounds of formula IIB, and salts and prodrugs thereof:

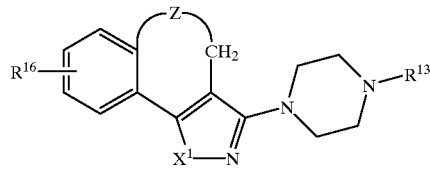

(IIB)

wherein $X^1$ represents oxygen or N—$R^{15}$;

Z is as defined with reference to formula I above; and $R^{13}$, $R^{15}$ and $R^{16}$ are as defined with reference to formula IIA above.

Particular values of $X^1$ include oxygen, NH and N-methyl.

A further sub-class of compounds according to the invention is represented by the compounds of formula IIC, and salts and prodrugs thereof:

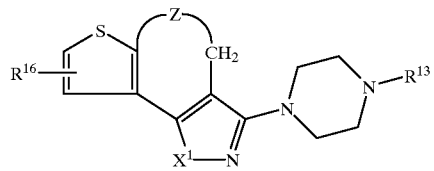

(IIC)

wherein

Z is as defined with reference to formula I above; and $X^1$, $R^{13}$ and $R^{16}$ are as defined with reference to formula IIA above.

Another particular sub-class of compounds according to the invention is represented by the compounds of formula IID, and salts and prodrugs thereof:

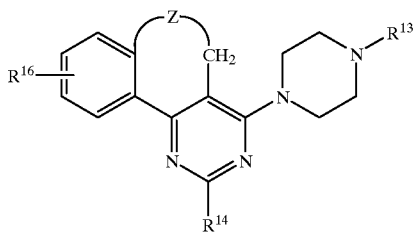

(11D)

wherein

Z is as defined with reference to formula I above;

$R^{13}$ represents $C_{2-6}$ alkenyl, $C_{3-7}$ cycloalkyl($C_{1-6}$)alkyl, aryl($C_{1-6}$)alkyl or heteroaryl($C_{1-6}$)alkyl, any of which groups may be optionally substituted;

$R^{14}$ represents $C_{1-6}$ alkyl, amino, $C_{1-6}$ alkylamino or di($C_{1-6}$)alkylamino; and $R^{16}$ represents hydrogen, halogen, tri-fluoromethyl, cyano, nitro, amino, $C_{1-6}$ alkylamino, di($C_{1-6}$) alkylamino, $C_{1-6}$ alkyl, $C_{1-6}$ alkoxy, aryl($C_{1-6}$)alkoxy or $C_{2-6}$ alkylcarbonyl.

Examples of suitable substituents on the group $R^{13}$ include one or more of $C_{1-6}$ alkyl, halogen, $C_{1-6}$ alkoxy and nitro.

Particular values of $R^{13}$ with reference to formula IID above include allyl, cyclopropylmethyl, cyclohexylmethyl, benzyl, methyl-benzyl, chlorobenzyl, dichlorobenzyl, methoxy-benzyl, nitro-benzyl, naphthylmethyl, phenethyl, phenylpropyl and aza-indolylmethyl.

A particular value of $R^{14}$ is amino.

Particular values of $R^{16}$ include hydrogen, methyl, ethyl, isopropyl, methoxy, benzyloxy, fluoro and chloro, especially hydrogen.

A further sub-class of compounds according to the invention is represented by the compounds of formula IIE, and salts and prodrugs thereof:

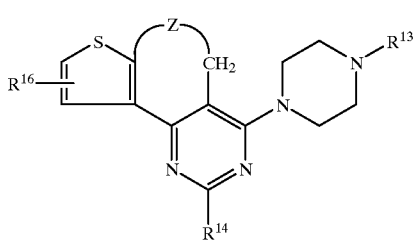

(11E)

wherein

Z is as defined with reference to formula I above; and $R^{13}$, $R^{14}$ and $R^{16}$ are as defined with reference to formula IID above.

Specific compounds within the scope of the present invention include:

3-[4-(2-phenylethyl)piperazin-1-yl]-4,5-dihydro-1H-benzo [g]indazole;

3-(4-benzylpiperazin-1-yl)-4,5-dihydro-1H-benzo[g] indazole;

3-[4-(1H-pyrrolo[2,3-b]pyridin-3-ylmethyl)piperazin-1-yl]-4,5-dihydro-1H-benzo[g]indazole;

3-(4-benzylpiperazin-1-yl)-4,5-dihydronaphth[1,2-c]-isoxazole;

3-[4-(2-phenylethyl)piperazin-1-yl]-4,5-dihydronaphth[1,2-c]isoxazole;

3-[4-(1H-pyrrolo[2,3-b]pyridin-3-ylmethyl)piperazin-1-yl]-4,5-dihydronaphth[1,2-c]isoxazole;

3-[4-(2-phenylethyl)piperazin-1-yl]-4,5-dihydro-2-methyl-2H-benzo[g]indazole:

3-[4-(2-phenylethyl)piperazin-1-yl]-4,5-dihydro-1-methyl-1H-benzo[g]indazole;

3-[4-(2-phenylethyl)piperazin-1-yl]-4,5-dihydro-1H-thieno [2,3-g]indazole;

3-(4-benzylpiperazin-1-yl)-1,4-dihydroindeno[1,2-c] pyrazole;

3-[4-(2-phenylethyl)piperazin-1-yl]-1,4-dihydroindeno[1,2-c]pyrazole;

3-(4-benzylpiperazin-1-yl)-1-methyl-1,4-dihydroindeno[1,2-c]pyrazole;

3-[4-(2-phenylethyl)piperazin-1-yl]-1-methyl-1,4-dihydroindeno[1,2-c]pyrazole;

3-[4-(1H-pyrrolo[2,3-b]pyridin-3-ylmethyl)piperazin-1-yl]-1-methyl-1,4-dihydroindeno[1,2-c]pyrazole;

4-(4-benzylpiperazin-1-yl)-5H-indeno[1,2-d]pyrimidin-2-ylamine;

4-[4-(2-phenylethyl)piperazin-1-yl]-5H-indeno[1,2-d] pyrimidin-2-ylamine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of disorders of the dopamine system, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention, wherein Q represents =N—NR$^5$—, —NR$^5$—N=, =N—O— or —O—N=, may be prepared by a process which comprises reacting a compound of formula III with a compound of formula IVa:

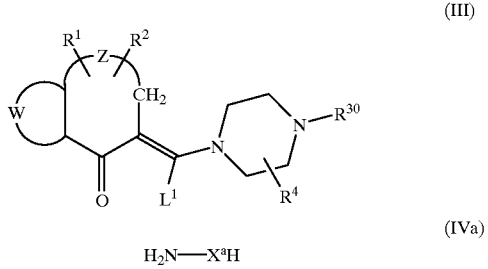

wherein W, Z, R$^1$, R$^2$ and R$^4$ are as defined above, R$^{30}$ corresponds to the group R$^3$ as defined above or represents an amino-protecting group, X$^a$ represents oxygen or N—R$^5$ in which R$^5$ is as defined above, and L$^1$ represents a suitable leaving group; followed, where necessary, by removal of the amino-protecting group R$^{30}$; and subsequently, if required, attachment of the substituent R$^3$ by conventional means.

The reaction is conveniently carried out by stirring the reactants in a suitable solvent, for example a C$_{1-4}$ alkanol such as ethanol or a mixture of N,N-dimethylformamide and methanol, optionally in the presence of a non-nucleophilic base such as ethyldiisopropylamine, suitably at room temperature.

Where the substituent R$^{30}$ represents an amino-protecting group, this group is suitably an acyl moiety such as t-butoxycarbonyl (BOC), which can conveniently be removed as necessary by treatment under acidic conditions, e.g. stirring in trifluoroacetic acid.

As will be appreciated, the overall reaction between compounds III and IVa will often give rise to a mixture of isomeric products of formula I, in one of which Q represents =N—NR$^5$— or =N—O—, and in the other of which Q represents —NR$^5$—N= or —O—N=. For this reason, it will generally be necessary at an appropriate stage to separate the mixture of isomers obtained therefrom by conventional methods such as column chromatography.

The compounds in accordance with the present invention, wherein Q represents =N—CR$^6$=N— may be prepared by a process which comprises reacting a compound of formula III with a compound of formula IVb:

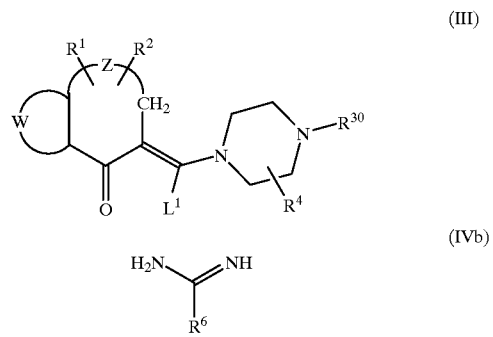

wherein W, Z, R$^1$, R$^2$, R$^4$ and R$^6$ are as defined above, R$^{30}$ corresponds to the group R$^3$ as defined above or represents an amino-protecting group, and L$^1$ represents a suitable leaving group; in the presence of a base; followed, where necessary, by removal of the amino-protecting group R$^{30}$; and subsequently, if required, attachment of the substituent R$^3$ by conventional means.

The reaction is conveniently carried out by heating the reactants in a suitable solvent, typically at the reflux temperature. The base employed will suitably be a C$_{1-4}$ alkoxide salt, in which case the reaction is conveniently effected in the corresponding C$_{1-4}$ alkanol as solvent. Typically, the reaction may be carried out in the presence of approximately two equivalents of sodium isopropoxide, utilising isopropanol as the solvent.

Where the substituent R$^{30}$ represents an amino-protecting group, this group is suitably an acyl moiety such as t-butoxycarbonyl (BOC), which can conveniently be removed as necessary by treatment under acidic conditions, e.g. stirring in trifluoroacetic acid.

The intermediates of formula III above may be prepared by reacting a compound of formula V with a compound of formula VI:

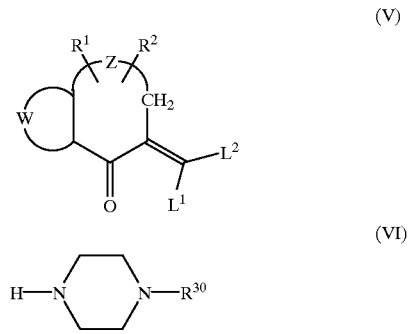

wherein W, Z, R$^1$, R$^2$, R$^{30}$ and L$^1$ are as defined above, and L$^2$ represents a suitable leaving group which may or may not be identical to L$^1$.

The reaction is conveniently effected by heating the reactants in an appropriate solvent, for example acetonitrile, suitably at the reflux temperature of the solvent employed.

The leaving groups $L^1$ and $L^2$, which may be the same or different, will suitably be conventional leaving groups well known from the art. For advantageous results, it has been found appropriate for $L^1$ and $L^2$ both to be $C_{1-4}$ alkylthio groups, especially methylthio.

Where $L^1$ and $L^2$ both represent $C_{1-4}$ alkylthio, the intermediates of formula V may be prepared by reacting a compound of formula VII:

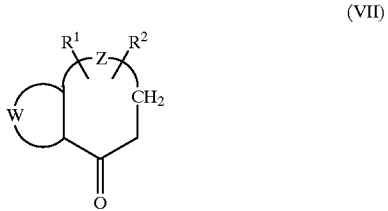

(VII)

wherein W, Z, $R^1$ and $R^2$ are as defined above; with carbon disulphide and an appropriate $C_{1-4}$ alkyl halide, e.g. methyl iodide, in the presence of a base such as sodium hydride.

The reaction is conveniently effected by stirring the reactants at room temperature in a suitable solvent, for example tetrahydrofuran.

Where they are not commercially available, the starting materials of formula VI and VII may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art. For example, a compound of formula I wherein $R^3$ is hydrogen initially obtained may be converted into a compound of formula I wherein $R^3$ represents $C_{1-6}$ alkyl by standard alkylation techniques, such as by treatment with an alkyl iodide, e.g. methyl iodide, typically under basic conditions, e.g. sodium hydride in N,N-dimethylformamide, or triethylamine in acetonitrile.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in organic Synthesis*, John Wiley & Sons, 1991. The protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 μM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [3H]-spiperone from the human dopamine $D_4$ receptor subtype of below 1.5 μM.

EXAMPLE 1

3-(4-(2-Phenylethyl)piperazin-1-yl)-4,5-dihydro-1H-benzo[g]indazole

Sodium hydride (60% in oil, 35 g, 880 mmol) was added with care to a solution of 1-tetralone (54 g, 370 mmol), carbon disulfide (27 ml, 33.7 g, 443 mmol), and methyl iodide (52 ml, 115 g, 810 mmol) in THF (400 ml) at 0° C. The mixture was stirred at room temperature overnight, giving a yellow solution with a white precipitate. Saturated aqueous ammonium chloride solution and ethyl acetate were added, the mixture separated, and the organic layer washed with water and brine, dried ($MgSO_4$), evaporated in vacuo, and the resulting solid recrystallised from ethyl acetate/hexanes to give 2-(bis-methylthiomethylene)-4,5-dihydro-2H-naphthalen-1-one (67 g, 59%) as yellow cubes, m.p. 54–56° C.; δ (360 MHz, $CDCl_3$) 2.43 (6H, br s, Me), 2.98 (2H, t, J=6.7 Hz, $CH_2$), 3.26 (2H, t, J=6.7 Hz, $CH_2$), 7.22 (1H, d, J=7.6 Hz, H-5), 7.32 (1H, t, J=7.6 Hz, H-7), 7.43 (1H, dt, J=1.2 and 7.6 Hz, H-6), 8.10 (1H, dd, J=1.2 and 7.6 Hz, H-8).

2-(Bis-methylthiomethylene)-4,5-dihydro-2H-naphthalen 1-one (11.56 g, 46 mmol) and 1-tert-butyloxycarbonylpiperazine (10.3 g, 55 mmol) were refluxed in acetonitrile (300 ml) for 24 h. The mixture was cooled, water (500 ml) added, and extracted with ethyl acetate (3×200 ml). The combined organics were washed with water and brine, dried (MgSO$_4$), evaporated in vacuo, and the resulting oil purified by flash chromatography, eluting with dichloromethane then dichloromethane:methanol (97:3 v/v) to give 2-(methylthio[4-(tert-butyloxycarbonyl)-1-piperazinyl]methylene)-4,5-dihydro-2H-naphthalen-1-one (8.75 g, 49%) as a foam; δ (360 MHz, CDCl$_3$) 1.49 (9H, s, $^t$Bu), 3.31 (3H, s, MeS), 2.86–2.94 (4H, m, CCH$_2$CH$_2$C), 3.3–3.5 (8H, m, NCH$_2$CH$_2$N), 7.18 (1H, d, J=7.5 Hz, H-5), 7.30 (1H, t, J=7.5 Hz, H-7), 7.37 (1H, dt, J=1.4 and 7.5 Hz, H-6), 8.10 (1H, dd, J=1.4 and 7.5 Hz, H-8).

2-(Methylthio[4-(tert-butyloxycarbonyl)-1-piperazinyl]methylene)-4,5-dihydro-2H-naphthalen-1-one (5.3 g, 13.7 mmol) and hydrazine hydrate (3.4 g, 68.5 mmol) were stirred in ethanol (100 ml) at room temperature for 16 h. The solvent was evaporated in vacuo, and the resulting oil purified by flash chromatography, eluting with dichloromethane:methanol (95:5 v/v) to give 3-(4-(tert-butyloxycarbonylpiperazin-1-yl)-4,5-dihydro-1H-benzo[g]indazole (3.9 g, 80%) as a yellow oil; δ (360 MHz, CDCl$_3$) 1.48 (9H, s, $^t$Bu), 2.72 (2H, t, J=7.7 Hz, CCH$_2$CH$_2$C), 2.95 (2H, t, J=7.7 Hz, CCH$_2$CH$_2$C), 3.13 (4H, t, J=5.2 Hz, NCH$_2$), 3.53 (4H, t, J=5.2 Hz, NCH$_2$), 7.2–7.4 (4H, m, ArH).

3-(4-(tert-Butyloxycarbonylpiperazin-1-yl)-4,5-dihydro-1H-benzo[g]indazole (1.65 g, 4.8 mmol) was dissolved in trifluoroacetic acid (10 ml). After 30 min the solvent was evaporated in vacuo to give 3-(piperazin-1-yl)-4,5-dihydro-1H-benzo[g]indazole bis-trifluoroacetate, which still contained an excess amount of trifluoroacetic acid (2.64 g), as a light brown solid; δ (360 Mhz, d$_6$-DMSO) 2.66 (2H, t, J=7.2 Hz, CCH$_2$CH$_2$C), 2.95 (2H, t, J=7.2 Hz, CCH$_2$CH$_2$C), 3.22 (4H, br s, NCH$_2$), 3.30 (4H, br s, NCH$_2$), 7.2–7.3 (3H, m, ArH), 7.56 (1H, d, J=6.6 Hz, H-9), 8.8 (2H, br s, NH$^+$). This was used crude in the next reaction.

3-(Piperazin-1-yl)-4,5-dihydro-1H-benzo[g]indazole bis-trifluoroacetate (416 mg, 1.1 mmol), ethyldiisopropylamine (590 μl, 430 mg, 3.3 mmol), and 2-phenethyl bromide (168 μl, 228 mg, 1.23 mmol) were heated in DMF (3 ml) at 60° C. for 4 h. The mixture was cooled, diluted with water (20 ml), extracted with ethyl acetate (3×10 ml), the combined organic fractions washed with brine, dried (MgSO$_4$), and evaporated in vacuo. The resulting light brown oil was dissolved in ethanol (2 ml), heated to boiling, and oxalic acid (1.3 ml of a 1M solution in ethanol) added. After cooling to room temperature the resulting solid was collected, washed with ethanol, and recrystallised from DMF:ethanol (1:9 v/v) to give 3-(4-(2-phenylethyl)piperazin-1-yl)-4,5-dihydro-1H-benzo[g]indazole oxalate salt (98 mg, 30% over two steps) as white needles mp 216–219° C. (Found: C, 66.55; H, 6.32; N, 12.30. C$_{23}$H$_{24}$N$_4$ C$_2$O$_4$H$_2$ requires C, 66.94; H, 6.29; N, 12.49%); δ (360 MHz, d$_6$-DMSO) 2.66 (2H, t, J=7.6 Hz, CCH$_2$CH$_2$C), 2.87 (2H, t, J=7.6 Hz, CCH$_2$CH$_2$C), 2.88 (2H, t J=7 Hz, PhCH$_2$), 3.1–3.2 (6H, m, CH$_2$), 3.25–3.4 (4H, m, CH$_2$), 7.1–7.4 (8H, m, ArH), 7.55 (1H, d, J=6.7 Hz, H-9); m/z (CI$^+$, NH$_3$) 359 (M$^+$+H).

EXAMPLE 2

3-(4-Benzylpiperazin-1-yl)-4,5-dihydro-1H-benzo[g]indazole oxalate salt, white microcrystalline solid, mp 254–256° C. (from EtOH) (Found: C, 65.71; H, 6.04; N, 12.40. C$_{22}$H$_{24}$N$_4$.C$_2$H$_2$O$_4$.0.25H$_2$O requires C, 65.66; H, 6.08; N, 12.76%); δ (360 MHz, d$_6$-DMSO) 2.63 (2H, t, =7.6 Hz, CCH$_2$CH$_2$C), 2.86 (2H, t, J=7.6 Hz, CCH$_2$CH$_2$C), 2.96 (4H, br s, NCH$_2$), 3.26 (4H, br s, NCH$_2$), 4.04 (2H, s, PhCH$_2$), 7.1–7.3 (3H, m, ArH), 7.4–7.5 (5H, m, ArH), 7.54 (1H, d, J=6.7 Hz, H-9); m/z (CI$^+$, NH$_3$) 345 (M$^+$+H).

EXAMPLE 3

3-(4-(1H-Pyrrolo[2,3-b]pyridin-3-ylmethyl)-piperazin-1-yl)-4,5-dihydro-1H-benzo[g]indazole 3-(Piperazin-1-yl)-4,5-dihydro-1H-benzo[g]indazole bis-trifluoroacetate (708 mg, 2 mmol), ethyldiisopropylamine (700 μl, 511 mg, 4 mmol) and 3-dimethylaminomethyl-1H-pyrrolo[2,3-b]pyridine (175 mg, 1 mmol) were heated in toluene (4 ml) and DMF (2 ml) at 100° C. for 3 h. The mixture was cooled, water (20 ml) added, and the mixture extracted with ethyl acetate (3×15 ml). The combined organic extracts were washed with brine, dried and evaporated in vacuo to give a brown solid, which was suspended in boiling methanol (4 ml), then cooled. The liquid was removed, and the solid recrystallised from aqueous methanol to give the title compound (53 mg, 7%) as a white microcrystalline solid, mp 245–247° C. (Found: C, 71.4; H, 6.35; N, 21.31. C$_{23}$H$_{24}$N$_6$.0.25H$_2$O requires C, 71.02; H, 6.35; N, 21.60%); δ (360 MHz, d$_6$-DMSO) 2.5–2.55 (4H, m, NCH$_2$), 2.61 (2H, t, J=7.5 Hz, CCH$_2$CH$_2$C), 2.84 (2H, t, J=7.5 Hz, CCH$_2$CH$_2$C), 3.05–3.10 (4H, m, NCH$_2$), 3.68 (2H, s, NCH$_2$C), 7.04 (1H, dd, J=4.7 and 7.8 Hz, NCHCH), 7.1–7.3 (3H, m, ArH), 7.37 (1H, s, CHNH), 7.52 (1H, d, J=7.8 Hz, CHCHCHN), 8.05 (1H, d, J=6.6 Hz, H-9), 8.19 (1H, d, J=4.7 Hz, NCHCH), 11.46 (1H, s, NH), 12.20 (1H, s, NH); m/z (CI$^+$, NH$_3$) 385 (M$^+$+H).

EXAMPLE 4

3-(4-Benzylpiperazin-1-yl)-4,5-dihydronaphth[1,2-c]isoxazole 2-(Methylthio[4-(tert-butyloxycarbonyl)piperazin-1-yl]methylene)-4,5-dihydro-2H-naphthalen-1-one (70 mg, 185 μmol), hydroxylamine hydrochloride (139 mg, 2 mmol) and ethyldiisopropylamine (350 μl, 256 mg, 2 mmol) were stirred in ethanol (2 ml) for 16 h. Water (10 ml) was added, and the mixture extracted with ethyl acetate (3×10 ml). The combined organic layers were washed with brine, dried, evaporated in vacuo, and purified by preparative thin layer chromatography to give 3-[3-(tert-Butyloxycarbonyl)piperazin-1-yl)-4,5-dihydronapth[1,2-c]isoxazole as a white solid (49 mg, 77%); δ (360 MHz, CDCl$_3$) 1.48 (9H, s, $^t$Bu), 2.78 (2H, t, J=7.9 Hz, CCH$_2$CH$_2$C), 3.04 (2H, t, J=7.9 Hz, CCH$_2$CH$_2$C), 3.29 (4H, t, J=5.4 Hz, NCH$_2$), 3.57 (4H, t, J=5.4 Hz, NCH$_2$), 7.2–7.3 (3H, m, ArH), 7.6–7.65 (1H, m, H-9). This was taken on in the same way as Example 1 to give the title compound as white cubes, mp 148–149° C. (from ethyl acetate) (Found: C, 76.12; H, 6.61; N, 11.99. C$_{22}$H$_{23}$NO requires C, 76.49; H, 6.71; N, 12.16%); δ (360 MHz, d$_6$-DMSO) 2.45–2.50 (4H, m, NCH$_2$, partially under DMSO peak), 2.75 (2H, t, J=7.5 Hz, CCH$_2$CH$_2$C), 2.99 (2H, t, J=7.5 Hz, CCH$_2$CH$_2$C), 3.22 (4H, t, J=4.8 Hz, NCH$_2$), 3.52 (2H, s, NCH$_2$Ph), 7.2–7.4 (8H, m, ArH), 7.50 (1H, d, J=7.6 Hz, H-9); m/z (CI$^+$, NH$_3$) 346 (M$^+$+H).

EXAMPLE 5

3-[4-(2-Phenylethyl)piperazin-1-yl]-4,5-dihydronaphth[1,2-c]isoxazole

Light brown crystals mp 134–136° C. (from ethyl acetate/hexanes) (Found: C, 75.78; H, 6.84; N, 11.56.

$C_{23}H_{25}N_3O.0.25H_2O$ requires C, 75.89; H, 7.06; N, 11.55%); δ (360 MHz, $d_6$-DMSO) 2.55–2.60 (6H, m, $CH_2$'s), 2.75–2.80 (4H, m, $CH_2$'s), 2.99 (2H, t, J=7.8 Hz, $CCH_2CH_2C$), 3.23 (4H, t, J=4.7 Hz, $NCH_2$), 7.1–7.4 (8H, m, ArH), 7.50 (1H, dd, J=2.1 and 6 Hz, H-9); m/z ($CI^+$, $NH_3$) 360 ($M^++H$).

EXAMPLE 6

3-[4-(1H-Pyrrolo[2,3-b]pyridin-3-ylmethyl)-piperazin-1-yl]-4,5-dihydronaphth[1,2-c]isoxazole White plates, mp 248–250° C. (from methanol) (Found: C, 71.26; H, 6.03; N, 17.81. $C_{23}H_{23}N_5O$ requires C, 71.66; H, 6.01; N, 18.17%); δ (360 MHz, $d_6$-DMSO) 2.45–2.50 (4H, m, $NCH_2$, partially obscured by DMSO), 2.74 (2H, t, J=7.8 Hz, $CCH_2CH_2C$), 3.20 (4H, t, J=4.4 Hz, $NCH_2$), 3.69 (2H, s, $NCH_2$), 7.04 (1H, dd, J=4.7 and 7.9 Hz, CHCHN), 7.25–7.35 (3H, m, ArH), 7.37 (1H, s, CHNH), 7.50 (1H, d, J=7.9 Hz, CHCHCHN), 8.05 (1H, d, J=6.6 Hz, H-9), 8.20 (1H, d, J=4.7 Hz, CHCHN), 11.47 (1H, s, NH); m/z ($CI^+$, $NH_3$) 386 ($M^++H$).

EXAMPLES 7 AND 8

3-(4-(2-Phenylethyl)piperazin-1-yl)-4,5-dihydro-2-methyl-2H-benzo[g]indazole and 3-(4-(2-Phenylethyl)piperazin-1-yl)-4,5-dihydro-1-methyl-1H-benzo[g]indazole 2-(Methylthio(4-(tert-butyloxycarbonyl)piperazin 1-yl) methylene-4,5-dihydro-2H-naphthalen-1-one (3.2 g, 8.2 mmol) and methylhydrazine (5 ml) were kept in ethanol (30 ml) for four days. Water (150 ml) was added, and the mixture extracted with ethyl acetate (3×50 ml). The combined organic layers were washed with brine, dried ($MgSO_4$), evaporated in vacuo, and purified by flash chromatography, eluting with hexane:ethyl acetate (4:1 v/v) to give 3-(4-(tert-butyloxycarbonyl)piperazin-1-yl)-4,5-dihydro-1-methyl-1H-benzo[g]indazole (342 mg, 11%) as a colourless oil; $^1H$ NMR (360 MHz, $CDCl_3$) δ 1.52 (9H, s, $^tBu$), 2.67 (2H, t, J=7.3 Hz, $CCH_2CH_2C$), 2.94 (2H, t, J=7.3 Hz, $CCH_2CH_2C$), 3.15 (4H, t, J=5.1 Hz, $NCH_2$), 3.61 (4H, t, J=5.1 Hz, $NCH_2$), 4.15 (3H, s, Me), 7.22–7.34 (3H, m, ArH), 7.55 (1H, d, J=7.7 Hz, H-9). Iradiation at δ 4.15 gave a positive nOe to the doublet at δ 7.55, and the reverse; and 3-(4-(tert-butyloxycarbonyl)piperazin-1-yl)-4,5-dihydro-2-methyl-2H-benzo[g]indazole (561 mg, 19%) as a white solid δ (360 MHz, $CDCl_3$) 1.54 (9H, s, $^tBu$), 2.86 (2H, t, J=7.8 Hz, $CCH_2CH_2C$), 2.95 (2H, t, J=7.8 Hz, $CCH_2CH_2C$), 3.08 (4H, t, J=4.9 Hz, $NCH_2$), 3.60 (4H, t, J=4.9 Hz, $NCH_2$), 7.20–7.30 (3H, m, ArH), 7.83 (1H, d, J=7.5 Hz, H-9).

These were taken on as for Example 1 to give 3-(4-(2-phenylethyl)piperazin-1-yl)-4,5-dihydro-2-methyl-2H-benzo[g]indazole oxalate salt, mp 244–245° C. (from ethanol) (Found: C, 66.94; H, 6.42; H, 11.71. $C_{24}H_{28}N_4.C_2H_2O_4.0.2H_2O$ requires C, 66.99; H, 6.57; N, 12.02%); δ (360 MHz, $d_6$-DMSO) 2.8–2.9(4H, m, $CCH_2CH_2C$), 2.90–2.95 (2H, m, $CH_2$), 3.1–3.2 (6H, m, $CH_2$'s), 3.2–3.25 (4H, m, $CH_2$'s), 3.69 (3H, s, Me), 7.1–7.4 (8H, m, ArH), 7.61 (1H, d, J=7.7 Hz, H-9); m/z ($CI^+$, $NH_3$) 373 ($M^++H$), and 3-(4-(2-phenylethyl)piperazin-1-yl)-4,5-dihydro-1-methyl-1H-benzo[g]indazole oxalate salt, mp 225–226° C. (from ethanol) (Found: C, 67.04; H, 6.66; N, 11.92. $C_{24}H_{28}N_4.C_2H_2O_4.0.2H_2O$ requires C, 66.99; H, 6.57; N, 12.01%); δ (360 MHz, $d_6$-DMSO) 2.56 (2H, t, J=7.7 Hz, $CCH_2CH_2C$), 2.83 (2H, t, J=7.7 Hz, $CCH_2CH_2C$), 2.95 (2H, t, J=8 Hz, $PhCH_2$), 3.1–3.2 (6H, m, $CH_2$'s), 3.25–3.35 (4H, m, $CH_2$'s), 3.95 (3H, s, Me), 7.2–7.4 (8H, m, ArH), 7.63 (1H, d, J=7.1 Hz, H-9); m/z ($CI^+$, $NH_3$) 373 ($M^++H$).

EXAMPLE 9

3-(4-(2-Phenylethyl)piperazin-1-yl)-4,5-dihydro-1H-thieno[2,3-g]indazole

Oxalate salt, white plates, mp 145–147° C. (from ethanol) (Found: C, 58.99; H, 5.73; N, 11.89. $C_{21}H_{24}N_4S.C_2H_2O_4.0.8H_2O$ requires C, 58.91; H, 5.93; N, 11.95%); δ (360 MHz, $d_8$-DMSO) 2.76 (2H, t, J=7.7 Hz, $CH_2$), 2.9–3.0 (4H, m, $CH_2$'s), 3.1–3.2 (6H, m, $CH_2$'s), 3.2–3.3 (4H, m, $CH_2$'s), 7.20–7.35 (6H, m, ArH), 7.39 (1H, d, J=5.1 Hz, ArH); m/z ($CI^+$, $NH_3$), 365 ($M^++H$).

EXAMPLE 10

3-(4-Benzylpiperazin-1-yl)-1,4-dihydroindeno[1,2-c]pyrazole

Off white crystals, mp 256–258° C. (from DMF/Ether) (Found: C, 64.40; H, 5.57; N, 12.86. $C_{21}H_{22}N_4.C_2H_2O_4.0.5H_2O$ requires C, 64.32; H, 5.87; N, 13.05%) δ (360 MHz, $d_6$-DMSO) 2.8–2.9 (4H, m, $CH_2N$), 3.3–3.4 (4H, m, $CH_2N$), 3.60 (2H, s, $ArCH_2$), 3.84 (2H, s, $ArCH_2N$), 7.23 (1H, t, J=7.4 Hz, ArH), 7.32 (1H, t, J=7.4 Hz, ArH), 7.36–7.52 (7H, m, ArH); m/z ($CI^+$, $NH_3$) 331 ($M^++H$).

EXAMPLE 11

3-(4-(2-Phenylethyl)piperazin-1-yl)-1,4-dihydroindeno[1,2-c]pyrazole

Oxalate salt, off white crystals, mp 212–214° C. (from methanol/ether) (Found: C, 65.58; H, 6.04; N, 12.34. $C_{22}H_{24}N_4.1.1.C_2H_2O_4$ requires C, 66.54; H, 5.95; N, 12.63%) δ (360 MHz, $d_6$-DMSO) 2.93–2.98 (2H, m, $ArCH_2CH_2$), 3.09–3.44 (6H, m, $ArCH_2CH_2$ and $NCH_2$), 3.4–3.5 (4H, m, $NCH_2$), 3.63 (2H, s, $ArCH_2Ar$), 7.21–7.35 (7H, m, ArH), 7.51 (2H, t, J=7.2 Hz, ArH m to $CH_2CH_2$) m/z ($CI^+$, $NH_3$) 345 ($M^++H$).

EXAMPLE 12

3-(4-Benzylpiperazin-1-yl)-1-methyl-1,4-dihydroindeno[1,2-c]pyrazole

Oxalate salt, pale yellow crystals, mp 216–220° C. (from ethanol) (Found: C, 63.09; H, 5.63; N, 11.74. $C_{22}H_{24}N_4.1.4.C_2H_2O_4$ requires C, 63.31; H, 5.74; N, 11.91%) δ (360 MHz, $d_6$-DMSO) 2.86 (1H, br s, $NCH_2CH_2$), 3.32 (4H, br s, $NCH_2CH_2$), 3.58 (2H, s, $ArCH_2C$), 3.90 (3H, s, Ce), 3.92 (2H, s, $ArCH_2N$), 7.24–7.43 (7H, m, ArH), 7.50 (1H, d, J=7.5 Hz, ArH), 7.68 (1H, d, J=7.5 Hz, ArH) m/z ($CI^+$, $NH_3$) 345 ($M^++H$). Regiochemistry of Me group determined by NOE experiment carried out on an earlier intermediate.

EXAMPLE 13

3-(4-(1-Phenylethyl)piperazin-1-yl)-1-methyl-1,4-dihydroindeno[1,2-c]pyrazole Pale yellow crystals, mp 138–139° C. (from ethanol) (Found: C, 76.87; H, 7.14; N, 15.47. $C_{23}H_{26}N_4$ requires C, 77.06; H, 7.31; N, 15.63%) δ (360 MHz, d$_6$-DMSO), 2.53–2.58 (6H, m, ArCH$_2$CH$_2$), 2.74–2.79 (2H, m, ArCH$_2$C), 3.19–3.22 (4H, m, NCH$_2$CH$_2$), 3.59 (2H, s, ArCH$_2$C), 3.89 (3H, s, CH$_3$), 7.16–7.36 (7H, m, ArH), 7.49 (1H, d, J=7.4 Hz, ArH), 7.67 (1H, d, J=7.4 Hz, ArH) m/z (CI$^+$, NH$_3$) 359 (M$^+$+H). Regiochemistry of Me group determined by NOE experiments carried out on an earlier intermediate.

EXAMPLE 14

3-(4-(1H-Pyrrolo[2,3-b]pyridin-3-ylmethyl) piperazin-1-yl)-1-methyl-4-dihydroindeno[1,2-c] pyrazole Pale yellow needles, mp 235–240° C. (from DMF) (Found: C, 70.85; H, 6.50; N, 21.61. C$_{23}$H$_{24}$N$_6$.0.3H$_2$O requires C, 70.85; H, 6.36; N, 21.55%) δ (360 MHz, d$_6$-DMSO) 2.49–2.51 (4H, m, NCH$_2$), 3.2 (4H, brs, NCH$_2$), 3.56 (2H, s, ArCH$_2$), 3.67 (2H, s, ArCH$_2$), 3.95 (3H, s, CH$_3$), 7.04 (1H, dd, J=7.8 Hz and J=4.7 Hz, NCHCHCH), 7.22 (1H, td, J=7.5 Hz and 1.1 Hz, ArH), 7.34 (1H, td, J=7.5 Hz and 1.1 Hz, ArH), 7.38 (1H, d, J=2.3 Hz, NHCH), 7.48 (1H, d, J=7.4 Hz, ArH), 7.66 (1H, d, J=7.4 Hz, ArH), 8.05 (1H, dd, J=7.8 and 1.3 Hz, NCHCHCH), 8.20 (1H, dd, J=4.7 Hz and 1.5 Hz, NCHCHCH), 11.4 (1H, br s, NH) m/z (CI$^+$, NH$_3$) 385 (M$^+$+H). Regiochemistry of Me group determined by NOE experiment carried out on an earlier intermediate.

EXAMPLE 15

3-(1-(4-(2-Phenylethyl)piperazinyl))-4,5-dihydro-6, 8-dimethyl-1H-benzo[g]indazole Cream coloured needles, m.p. 177–179° C. (from EtOH-Hexane) (Found: C, 76.9; H, 7.8; N, 14.2. C$_{25}$H$_{30}$N$_4$.0.2 (H$_2$O) requires C, 77.0; H, 7.9; N, 14.4%). δ$_H$ (360 MHz; CDCl$_3$) 2.29 (3H, s, ArMe), 2.30 (3H, s, ArMe), 2.65–2.77 (8H, m, 3×NCH$_2$ and ArCH$_2$), 2.83–2.88 (4H, m, 2×ArCH$_2$), 3.31 (4H, t, J=5 Hz, 2×NCH$_2$), 6.92 (1H, s, ArH), 7.06 (1H, broad s, ArH) and 7.18–7.31 (5H, m, Ph); m/z (CI$^+$; NH$_3$) 387 (M$^+$+H).

EXAMPLE 16

3-(1-(4-(2-(3-Phenylpropyl))piperazinyl))-4,5-dihydro-1H-benzo[g]indazole

White amorphous solid, m.p. 170–172° C. (from EtOH) (Found: C, 59.6; H, 5.9; N, 10.0. C$_{24}$H$_{28}$N$_4$.2(CO$_2$H)$_2$.0.67 (H$_2$O) requires C, 59.6; H, 6.0; N, 9.9%). δ$_H$ (360 MHz; DMSO+CF$_3$CO$_2$H) 1.17 (3H, d, J=7 Hz, NCHCH$_3$), 2.70–2.78 (3H, m, NCHCH$_3$ and ArCH$_2$), 2.95 (2H, t, J=7 Hz, ArCH$_2$), 3.22–3.48 (4H, m, 2×NCH$_2$), 3.56–3.90 (6H, m, 2×NCH$_2$ and ArCH$_2$), 7.30–7.40 (8H, m, 8 of ArH), 7.64 (1H, d, J=6 Hz, 1 of ArH) and 9.90 (1H, broad s, NH); m/z (CI$^+$; NH$_3$) 390 (M$^+$+NH$_4$), 373 (M$^+$+H).

EXAMPLE 17

3-(4-(2-Phenylethyl)piperazin-1-yl)-1,4,5,6-tetrahydro-1,2-diazabenzo[e]azulene

White needles, m.p. 147–148° C. (from ethyl acetate:hexane) (Found: C, 76.56; H, 7.62; N, 14.80. C$_{24}$H$_{28}$N$_4$.0.2(H$_2$O) requires C, 76.64; H, 7.61; N, 14.90). δ (360 MHz; δ$_6$-DMSO) 1.89 (2H, quintet, J=5 Hz, CH$_2$CH$_2$CH$_2$), 2.55–2.7 (10H, m, CH$_2$'s), 2.76–2.82 (2H, m, CH$_2$), 3.00–3.05 (2H, m, CH$_2$), 3.25–3.35 (2H, m, CH$_2$), 7.1–7.25 (8H, m, ArH), 7.69 (1H, d, J=7 Hz, H-10), 12.1 (1H, s, NH); m/z (CI$^+$; NH$_3$) 373 (M$^+$+H).

EXAMPLE 18

1-Ethyl-3-(4-(2-phenylethyl)piperazin-1-yl)-4,5-dihydrobenzo[g]indazole

Oxalate salt, white solid, m.p. 193–195° C. (from ethanol) (Found: C, 66.91; H, 6.49; N, 10.98. C$_{25}$H$_{30}$N$_4$.1.2(C$_2$H$_2$O$_4$) requires C, 66.54; H, 6.60; N, 11.33%). δ$_H$ (360 MHz; δ$_6$-DMSO) 1.35 (3H, t, J=7.2 Hz, CH$_3$), 2.58–2.64 (2H, m, CH$_2$), 2.80–2.90 (2H, m, CH$_2$), 2.95–3.00 (2H, m, CH$_2$), 3.1–3.4 (10H, m, CH$_2$'s), 4.28 (2H, q, J=7.2 Hz, CH$_2$CH$_3$), 7.2–7.4 (8H, m, ArH), 7.51 (1H, d, J=7.8 Hz, ArH-9); irradiation of the signal at 4.28 gives a positive nOe to the signal at 7.51 ppm; m/z (CI$^+$; NH$_3$) 387 (M$^+$+H).

EXAMPLE 19

3-(4-(2-(5-Methylfuran-2-yl)ethyl)piperazin-1-yl)-4, 5-dihydrobenzo[g]indazole 5-methyl furan-2-acetic acid To a solution of potassium cyanide (12.2 g, 0.187 mol) and sodium carbonate (36 g, 0.338 mol) in water (250 ml) was added 5-methyl furfural (7.5 ml, 75 mmol) in 1,4-dioxane (12 ml) followed by glyoxal busulphite (3.0 g, 0.289 mol) and water (240 ml). After stirring for 2½ hr at room temperature, the reaction was worked up by adding 5N HCl$_{(aq)}$ to the reaction mixture carefully (HCN↑) until the pH fell to ≈1–2. Stirring was continued for 1 hr after which time, no more gas was evolved.

Products were extracted with chloroform (3×150 ml). Combined organics were washed with brine before being dried over Na$_2$SO$_4$ and concentrated in vacuo.

A brown solid was afforded (8.1 g, 78%). δ$_H$ (250 MHz, CDCl$_3$), 2.26 (3H, s, ArCH$_3$), 3.66 (2H, s, ArCH$_2$), 5.90 (1H, d, J=5 Hz, ArH), 6.12 (1H, d, J=5 Hz, ArH).

3-(4-(5-methylfuranyl)acetylpiperazin-1-yl)-4,5-dihydro-1H-benzo[g]indazole

To a solution of 3-piperazin-1-yl-4,5-dihydro-1H-benzo [g]indazole bistrifluoroacetate (450 mg, 0.94 mmol) and Hünigs base (664 μl, 3.76 mmol) in dichloromethane (25 ml), was added 5-methylfuranyl-2-acetic acid (131 mg, 0.94 mmol), 1-(3-dimethylaminopropyl)-3-ethylcarbodiimide hydrochloride (200 mg, 1.04 mmol) and hydroxybenzotriazole (140 mg, 1.04 mmol). The reaction was stirred for 4 hr at room temperature under nitrogen. The reaction mixture was poured into sodium bicarbonate solution and extracted with ethyl acetate (2×50 ml). The combined organics were washed with water and brine before being dried over Na$_2$SO$_4$ and concentrated in vacuo. The residue was chromatographed through silica eluting with 5% MeOH/DCM/ 1% NH$_{3(aq)}$ (v/v) to give the title compound as a pale brown crystalline solid (180 mg, 51%). δH (250 MHz, d$_6$-DMSO), 2.24 (3H, s, ArCH$_3$), 2.65 (2H, t, J=3.8 Hz, CCH$_2$CH$_2$C), 2.65 (2H, t, J=3.8 Hz, CCH$_2$CH$_2$C), 3.05 (4H,br s, NCH$_2$CH$_2$N), 3.64 (4H, br s, NCH$_2$CH$_2$N), 3.74 (2H, s, ArCH$_2$C), 5.98 (1H, d, J=5 Hz, ArCH), 6.06 (1H, d, J=5 Hz, ArH), 7.14–7.33 (3H, m, ArH), 7.52 (1H, d, J=7.0 Hz, ArH), 12.40 (1H, br s, NH).

3-(4-(2-(5-Methylfuran-2-yl)ethyl)piperazin-1-yl)-4,5-dihydrobenzo[g]indazole

To a solution of 3-(4-(5-methylfuranyl)acetyl piperazin-1-yl)4,5-dihydro-1H-benzo[g]indazole (170 mg), 0.45 mmol) in tetrahydrofuran (25 ml) was added LiAlH$_4$ (1.0M in THF) (680 μl, 0.68 mmol) slowly at room temperature under N$_2$. Stirring was continued for 1 hr.

Reaction mixture was worked up by cautious addition of 20% NaOH(aq) until no further gas was evolved. More water was then added (30 ml) and the mixture extracted with ethyl acetate (2×50 ml). Combined organics were washed with water and brine before being dried over Na$_2$SO$_4$ and concentrated in vacuo. The oily residue was chromatographed on silica preparative TLC plates eluting with 4% MeOH/DCM/1% NH(aq) (v/v) to give purified title compound. (104 mg,≈99%) as pale yellow crystals, m.p. 150–152° C. (Found; C, 71.95; H, 7.37; N, 15.01. C$_{22}$H$_{26}$N$_4$O.0.3(H$_2$O) requires C, 71.83; H, 7.29; N, 15.23%); δH (360 MHz, d$_6$-DMSO), 2.21 (3H, s, OCCH$_3$), 2.44–2.66 (4H, m, CH$_2$), 2.74 (2H, tr, J=7.4 Hz, CH$_2$), 2.86 (2H, t, J=7.4 Hz, CH$_2$), 3.08 (4H, br s, NCH$_2$), 5.93 (1H, s, OCCH), 5.98 (1H, s, OCCH), 7.15–7.27 (3H, m, ArH), 7.52 (1H, br d, J=7.0 Hz, ArH), 12.23 (1H, br s, NH) m/z (CI$^+$, NH$_3$) 363 (M$^+$+H).

EXAMPLE 20

2-Methyl-3-(4-(2-phenylethyl)piperazin-1-yl)-4,5,6-tetrahydro-1,2-diazabenzo[e]azulene Oxalate salt, white crystals, m.p. 225–228° C. (from ethanol) (Found; C, 68.28; H, 6.73; N, 11.61. C$_{25}$H$_{30}$N$_4$.(COOH)$_2$ requires C, 68.05; H, 6.77; N, 11.76%); δH (360 MHz, d$_6$-DMSO), 1.94 (2H, m, CH$_2$CH$_2$CH$_2$), 2.75 (4H, m, CH$_2$), 2.94 (2H, m, CH$_2$), 3.10 (6H, m, CH$_2$), 3.27 (4H, br s, CH$_2$), 3.72 (3H, s, NCH$_3$), 7.14–7.36 (8H, m, ArH), 7.87 (1H, d, J=7.3 Hz, ArH) m/z (CI$^+$, NH$_3$) 387 (M$^+$+H).

EXAMPLE 21

3-(4-(2-(2-Chlorophenyl)ethyl)piperazin-1-yl)-4,5-dihydrobenzo[g]indazole

Oxalate salt, pale yellow hexagonal plates, m.p. 134–136° C. (from ethanol) (Found; C, 61.58; H, 5.61; N, 11.33. C$_{23}$H$_{25}$N$_4$Cl. (COOH)$_2$.0.2 H$_2$O requires C, 61.71; H, 5.68; N, 11.51%); δH (360 MHz, d$_6$-DMSO), 2.66 (2H, t, J=8.0 Hz, CH$_2$), 2.88 (2H, t, J=8.0 Hz, CH$_2$), 3.03–3.07 (8H, m, CH$_2$), 3.27 (4H, br s, CH$_2$), 7.19–7.47 (7H, m, ArH), 7.55 (1H, d, J=6.5, ArH) m/z (CI$^+$, NH$_3$) 393 (M$^+$+H).

EXAMPLE 22

3-(4-(1,2,3,4-Tetrahydronaphthy-2-yl)piperazin-1-yl)-4,5-dihydro-1H-benzo[g]indazole Oxalate salt, pale pink crystals, m.p. 208–210° C. (from ethanol) (Found; C, 61.39; H, 5.72; N, 10.26. C$_{25}$H$_{28}$N$_4$.2(COOH)$_2$ requires C, 61.69; H, 5.71; N, 9.92%); δH (360 MHz, d$_6$-DMSO), 1.78–1.80 (1H, in, CH$_A$H$_B$), 2.31 (1H, br s, CH$_A$H$_B$), 2.67 (2H, t, J=7.2 Hz, CH$_2$), 2.83–3.07 (5H, m, CH$_2$), 3.17–3.20 (1H, m, CH), 3.39–3.57 (9H, m, CH$_2$), 7.15–7.30 (7H, m, ArH), 7.56 (1H, d, J=7.2 Hz, ArH) m/z (CI$^+$, NH$_3$) 385 (M$^+$+H).

EXAMPLE 23

4-(4-Benzylpiperazin-1-yl)-5H-indeno[1,2-d]pyrimidin-2-ylamine

To dry isopropyl alcohol (10 ml) was added sodium metal (154 mg, 6.7 mmol) and the mixture refluxed under N$_2$ until all of the sodium had dissolved (≈0.5 h). To this solution was then added guanidine hydrochloride (64.3 ml, 6.7 mmol) and the suspension refluxed for a further 0.5 h. Meanwhile, 2-(methylthio[4-(tert-butyloxycarbonyl)-1-piperazinyl) methylene-indan-1-one (500 mg, 1.34 mmol) was dissolved in isopropylalcohol (3 ml) and after 0.5 h was added, in solution, to the refluxing suspension. The reaction was refluxed for 4 h and then stirred at room temperature for 16 h. Work-up of the reaction was performed by pouring the mixture into saturated sodium bicarbonate solution (150 ml) and extracting the products into ethyl acetate (2×50 ml). The organic layer was then separated and washed with water and brine before being dried over Na$_2$SO$_4$ and concentrated in vacuo. The residues were chromatographed upon flash silica eluting with dichloromethane:methanol (95:5 v/v) to give a pale yellow foam, 5 (250 MHz, CDCl$_3$) 1.50 (9H, s, C(CH$_3$)$_3$), 3.52–3.58 (4H, m, NCH$_2$), 3.80–3.86 (4H, m, NCH$_2$), 3.90 (2H, s, ArCH$_2$), 4.8 (2H, br s, NH$_2$), 7.44–7.48 (2H, m, ArH), 7.55–7.58 (1H, m, ArH), 7.98–8.02 (1H, m, ArH). This was deprotected with trifluoroacetic acid and then N-benzylated with benzyl bromide to give the title compound as pale yellow crystals, mp 175–180° C. (from ethanol) (Found: C, 70.74; H, 6.28; N, 18.46. C$_{22}$H$_{23}$N$_5$.0.8H$_2$O requires C, 71.06; H, 6.67; N, 18.83%) δ (360 MHz, 353K, d$_6$-DMSO) 2.53 (4H, m, NCH$_2$CH$_2$), 3.56 (2H, s, ArCH$_2$C), 3.80 (4H, NCH$_2$CH$_2$), 3.93 (2H, s, ArCH$_2$N), 5.8 (2H, br s, NH$_2$), 7.25–7.44 (7H, m, ArH), 7.55 (1H, d, J=6.7 Hz, ArH), 7.78 (1H, d, J=7.6 Hz, ArH) m/z (CI$^+$, NH$_3$) 358 (M$^+$+H).

EXAMPLE 24

4-(4-(2-Phenylethyl)piperazin-1-yl)-5H-indeno[1,2-d]pyrimidin-2-ylamine

Pale yellow crystals, mp 122–124° C. (from ethanol) (Found: C, 73.57; H, 6.60; N, 18.49. C$_{23}$H$_{25}$N$_5$.0.8H$_2$O requires C, 73.65; H, 6.82; N, 18.67%) δ$_H$ (360 MHz, d$_6$-DMSO) 2.51–2.59 (6H, m, ArCH$_2$CH$_2$ and NCH$_2$CH$_2$), 2.76–2.80 (2H, m, ArCH$_2$CH$_2$N), 3.76–3.79 (4H, m, NCH$_2$CH$_2$), 3.96 (3H, s, ArCH$_2$C), 6.04 (2H, br s, NH$_2$), 7.16–7.31 (5H, m, ArH), 7.38–7.46 (2H, m, ArH), 7.57 (1H, d, J=6.5 Hz, ArH), 7.75 (1H, dd, J=6.6 Hz and 2.1 Hz, ArH) m/z (CI$^+$, NH$_3$) 327 (M$^+$+H).

We claim:

1. A compound of formula I, or a salt thereof or a prodrug thereof:

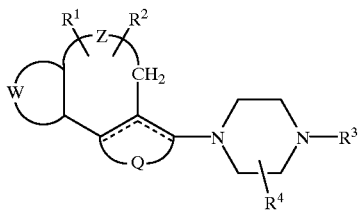
(I)

wherein the broken line represents a double bond whereby the ring containing Q is heteroaromatic;

W is selected from the group consisting of phenyl or 2,3-thienyl, which ring can be substituted by one or more substituents selected from the group consisting of: halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl;

Q is selected from =N—$NR^5$—, —$NR^5$—N=, =N—O—, —O—N= and =N—$CR^6$=N—;

Z represents a chemical bond, or a methylene or ethylene group;

$R^1$, $R^2$ and $R^5$ independently represent hydrogen or $C_{1-6}$ alkyl;

one of $R^3$ and $R^4$ represents hydrocarbon, selected from the group consisting of: $C_{2-6}$ alkenyl, $C_{3-7}$ cycloalkyl ($C_{1-6}$)alkyl, aryl($C_{1-6}$)alkyl and heteroaryl($C_{1-6}$)alkyl, wherein heteroaryl is selected from the group consisting of: pyridyl, quinolyl, isoquinolyl, pyridazinyl, pyrimidinyl, pyrazinyl, pyrazinyl, furyl, benzofuryl, dibenzofuryl, thienyl, benzthienyl, indolyl, aza-indolyl, imidazolyl, oxadiazolyl and thiadiazolyl; or a heterocyclic group selected from the group consisting of: azetidinyl, pyrrolidyl, piperidyl, piperazinyl and morpholinyl; in which each $R^3$ and $R^4$ substitutent can be substituted by $C_{1-6}$ alkyl, halogen, $C_{1-6}$ alkoxy or nitro, and the other of $R^3$ and $R^4$ represents hydrogen, hydrocarbon or a heterocyclic group, as defined above; and $R^6$ represents $C_{1-6}$alkyl or —$NR^aR^b$, in which $R^a$ and $R^b$ independently represent hydrogen or $C_{1-6}$alkyl.

2. A compound as claimed in claim 1 represented by formula (IA), and pharmaceutically acceptable salts and prodrugs thereof:

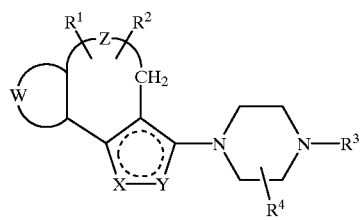
(IA)

wherein the broken circle represents two non-adjacent double bonds whereby the five-membered ring containing X and Y is aromatic;

W represents the residue of an optionally substituted aromatic or heteroaromatic ring;

one of X and Y represents nitrogen, and the other of X and Y represents oxygen or N—$R^5$;

Z represents a chemical bond, or a methylene or ethylene group;

$R^1$, $R^2$ and $R^5$ independently represent hydrogen or $C_{1-6}$ alkyl; and one of $R^3$ and $R^4$ represents hydrocarbon or a heterocyclic group, and the other of $R^3$ and $R^4$ represents hydrogen, hydrocarbon or a heterocyclic group.

3. A compound as claimed in claim 1 represented by formula (IB), and pharmaceutically acceptable salts and prodrugs thereof:

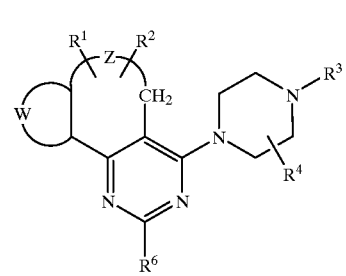
(IB)

wherein

W represents the residue of an optionally substituted aromatic or heteroaromatic ring;

Z represents a chemical bond, or a methylene or ethylene group;

$R^1$ and $R^2$ independently represent hydrogen or $C_{1-6}$ alkyl;

one of $R^3$ and $R^4$ represents hydrocarbon or a heterocyclic group, and the other of $R^3$ and $R^4$ represents hydrogen, hydrocarbon or a heterocyclic group; and $R^6$ represents $C_{1-6}$ alkyl or —$NR^aR^b$, in which $R^a$ and $R^b$ independently represent hydrogen or $C_{1-6}$ alkyl.

4. A compound as claimed in claim 1 represented by formula IIA, and salts and prodrugs thereof:

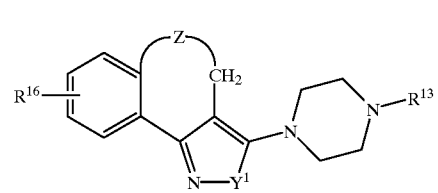
(11A)

wherein

Z represents a chemical bond, or a methylene or ethylene group;

$Y^1$ represents oxygen or N—$R^{15}$;

$R^{13}$ represents $C_{2-6}$ alkenyl, $C_{3-7}$ cycloalkyl($C_{1-6}$)alkyl, aryl($C_{1-6}$)alkyl or heteroaryl($C_{1-6}$)alkyl, any of which groups may be optionally substituted;

$R^{15}$ represents hydrogen or $C_{1-6}$ alkyl; and $R^{16}$ represents hydrogen, halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl.

5. A compound as claimed in claim 1 represented by formula IIB, and salts and prodrugs thereof:

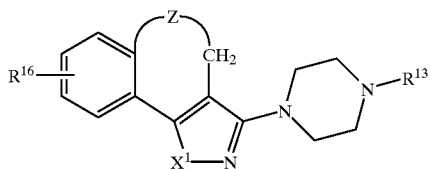

(11B)

wherein
- $X^1$ represents oxygen or N—$R^{15}$;
- Z represents a chemical bond, or a methylene or ethylene group; and
- $R^{13}$ represents $C_{2-6}$ alkenyl, $C_{3-7}$ cycloalkyl($C_{1-6}$)alkyl, aryl($C_{1-6}$)alkyl or heteroaryl($C_{1-6}$)alkyl, any of which groups may be optionally substituted by $C_{1-6}$alkyl, halogen, $C_{1-6}$alkoxy and nitro;
- $R^5$ represents hydrogen or $C_{1-6}$ alkyl; and
- $R^{16}$ represents hydrogen, halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl.

6. A compound as claimed in claim 1 represented by formula IIC, and salts and prodrugs thereof:

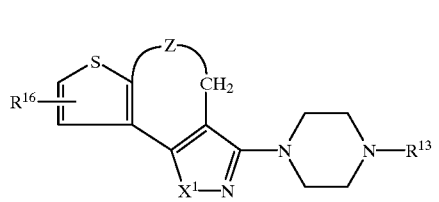

(IIC)

wherein
- Z represents a chemical bond, or a methylene or ethylene group; and
- $R^{13}$ represents $C_{2-6}$ alkenyl, $C_{3-7}$ cycloalkyl($C_{1-6}$)alkyl, aryl($C_{1-6}$)alkyl or heteroaryl($C_{1-6}$)alkyl, any of which groups may be optionally substituted by $C_{1-6}$alkyl, halogen, $C_{1-6}$alkoxy and nitro; and
- $R^{16}$ represents hydrogen, halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl and
- $X^1$ represents oxygen or N—$R^{15}$, wherein $R^{15}$ represents hydrogen or $C_{1-6}$alkyl.

7. A compound as claimed in claim 1 represented by formula IID, and salts and prodrugs thereof:

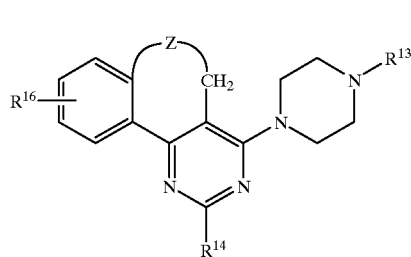

(IID)

wherein
- Z represents a chemical bond, or a methylene or ethylene group; and
- $R^{13}$ represents $C_{2-6}$ alkenyl, $C_{3-7}$ cycloalkyl($C_{1-6}$)alkyl, aryl($C_{1-6}$)alkyl or heteroaryl($C_{1-6}$)alkyl, any of which groups may be optionally substituted;
- $R^{14}$ represents $C_{1-6}$ alkyl, amino, $C_{1-6}$ alkylamino or di($C_{1-6}$)alkylamino; and
- $R^{16}$ represents hydrogen, halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl.

8. A compound as claimed in claim 1 represented by formula IIE, and salts and prodrugs thereof:

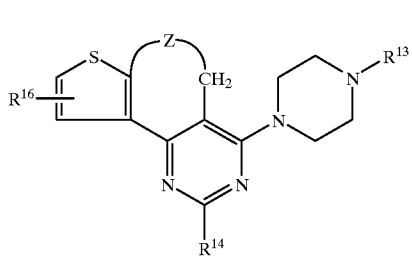

(IIE)

wherein
- Z represents a chemical bond, or a methylene or ethylene group; and
- $R^{13}$ represents $C_{2-6}$ alkenyl, $C_{3-7}$ cycloalkyl($C_{1-6}$)alkyl, aryl($C_{1-6}$)alkyl or heteroaryl($C_{1-6}$)alkyl, any of which groups may be optionally substituted;
- $R^{14}$ represents $C_{1-6}$ alkyl, amino, $C_{1-6}$ alkylamino or di($C_{1-6}$)alkylamino; and
- $R^{16}$ represents hydrogen, halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl.

9. A compound selected from:

3-[4-(2-phenylethyl)piperazin-1-yl]-4,5-dihydro-1H-benzo[g]indazole;

3-(4-benzylpiperazin-1-yl)-4,5-dihydro-1H-benzo[g]indazole;

3-[4-(1H-pyrrolo[2,3-b]pyridin-3-ylmethyl)piperazin-1-yl]-4,5-dihydro-1H-benzo[g]indazole;

3-(4-benzylpiperazin-1-yl)-4,5-dihydronaphth[1,2-c]-isoxazole;

3-[4-(2-phenylethyl)piperazin-1-yl]-4,5-dihydronaphth[1,2-c]isoxazole;

3-[4-(1H-pyrrolo[2,3-b]pyridin-3-ylmethyl)piperazin-1-yl]-4,5-dihydronaphth[1,2-c]isoxazole;

3-[4-(2-phenylethyl)piperazin-1-yl]-4,5-dihydro-2-methyl-2H-benzo[g]indazole;

3-[4-(2-phenylethyl)piperazin-1-yl]-4,5-dihydro-1-methyl-1H-benzo[g]indazole;

3-[4-(2-phenylethyl)piperazin-1-yl]-4,5-dihydro-1H-thieno[2,3-g]indazole;

3-(4-benzylpiperazin-1-yl)-1,4-dihydroindeno[1,2-c]pyrazole;

3-[4-(2-phenylethyl)piperazin-1-yl]-1,4-dihydroindeno[1,2-c]pyrazole;

3-(4-benzylpiperazin-1-yl)-1-methyl-1,4-dihydroindeno[1,2-c]pyrazole;

3-[4-(2-phenylethyl)piperazin-1-yl]-1-methyl-1,4-dihydroindeno[1,2-c]pyrazole;

3-[4-(1H-pyrrolo[2,3-b]pyridin-3-ylmethyl)piperazin-1-yl]-1-methyl-1,4-dihydroindeno[1,2-c]pyrazole;

4-(4-benzylpiperazin-1-yl)-5H-indeno[1,2-d]pyrimidin-2-ylamine;

4-[4-(2-phenylethyl)piperazin-1-yl]-5H-indeno[1,2-d]pyrimidin-2-ylamine;

and pharmaceutically acceptable and prodrugs thereof.

10. A pharmaceutical composition comprising a compound as claimed in claim 1 in association with a pharmaceutically acceptable carrier.

11. A process for the preparation of a compound as claimed in claim 1, wherein Q represents =N—NR$^5$—, —NR$^5$—N=, =N—O— or —O—N=, which comprises reacting a compound of formula III with a compound of formula IVa:

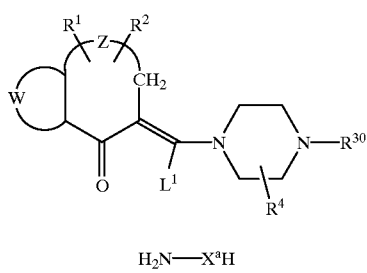

(III)

H$_2$N—X$^a$H     IVa wherein W is selected from the group consisting of phenyl, or 2,3-thienyl which ring can be substituted by one or more substituents selected from the group consisting of: halogen, trifluoromethyl, cyano, nitro, amino, C$_{1-6}$ alkylamino, di(C$_{1-6}$)alkylamino, C$_{1-6}$ alkyl, C$_{1-6}$ alkoxy, aryl(C$_{1-6}$)alkoxy and C$_{2-6}$ alkylcarbonyl;

Z represents a chemical bond, or a methylene or ethylene group;

R$^1$, R$^2$ independently represent hydrogen or C$_{1-6}$ alkyl;

R$^4$ represents hydrogen, hydrocarbon, selected from the group consisting of: C$_{2-6}$ alkenyl, C$_{3-7}$ cycloalkyl(C$_{1-6}$)alkyl, aryl(C$_{1-6}$)alkyl and heteroaryl(C$_{1-6}$)alkyl, wherein heteroaryl is selected from the group consisting of: pyridyl, quinolyl, isoquinolyl, pyridazinyl, pyrimidinyl, pyrazinyl, pyrazinyl, furyl, benzofuryl, dibenzofuryl, thienyl, benzthienyl, indolyl, aza-indolyl, imidazolyl, oxadiazolyl and thiadiazolyl, which can be substituted by C$_{1-6}$ alkyl, halogen, C$_{1-6}$ alkoxy or nitro;

or a heterocyclic group selected from the group consisting of: azetidinyl, pyrrolidyl, piperidyl, piperazinyl and morpholinyl groups; and R$^{30}$ corresponds to the group R$^3$ as defined in claim 1 or represents an amino-protecting group, X$^a$ represents oxygen or N—R$^5$ in which R$^5$ is or hydrogen or C$_{1-6}$alkyl, and L$^1$ represents a suitable leaving group.

12. A process for the preparation of a compound as claimed in claim 1, wherein Q represents =N—CR$^6$=N—, which comprises reacting a compound of formula III with a compound of formula IVb:

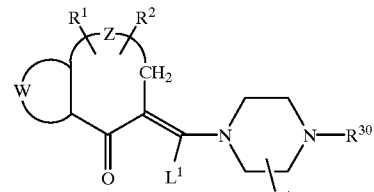

(III)

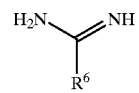

(IVb)

wherein W is selected from the group consisting of phenyl, or 2,3-thienyl, which ring can be substituted by one or more substituents selected from the group consisting of: halogen, trifluoromethyl, cyano, nitro, amino, C$_{1-6}$ alkylamino, di(C$_{1-6}$)alkylamino, C$_{1-6}$ alkyl, C$_{1-6}$ alkoxy, aryl(C$_{1-6}$) alkoxy and C$_{2-6}$ alkylcarbonyl;

Z represents a chemical bond, or a methylene or ethylene group;

R$^1$, R$^2$ independently represent hydrogen or C$_{1-6}$ alkyl;

and R$^4$ represents hydrogen, hydrocarbon, selected from the group consisting of: C$_{2-6}$ alkenyl, C$_{3-7}$ cycloalkyl (C$_{1-6}$)alkyl, aryl(C$_{1-6}$)alkyl and heteroaryl(C$_{1-6}$)alkyl, wherein heteroaryl is selected from the group consisting of: pyridyl, quinolyl, isoquinolyl, pyridazinyl, pyridazinyl, pyrazinyl, pyrazinyl, furyl, benzofuryl, dibenzofuryl, thienyl, benzthienyl, indolyl, aza-indolyl, imidazolyl, oxadiazolyl and thiadiazolyl, which can be substituted by C$_{1-6}$ alkyl, halogen, C$_{1-6}$ alkoxy or nitro, or a heterocyclic group selected from the group consisting of: azetidinyl, pyrrolidyl, piperidyl, piperazinyl and morpholinyl groups; and R$^6$ represents C$_{1-6}$alkyl or —NR$^a$R$^b$, in which R$^a$ and R$^b$ independently represent hydrogen or C$_{1-6}$alkyl; R$^{30}$ corresponds to the group R$^3$ which represents hydrogen, hydrocarbon, selected from the group consisting of: C$_{2-6}$ alkenyl, C$_{3-7}$ cycloalkyl(C$_{1-6}$)alkyl, aryl(C$_{1-6}$)alkyl and heteroaryl(C$_{1-6}$)alkyl, wherein heteroaryl is selected from the group consisting of: pyridyl, quinolyl, isoquinolyl, pyridazinyl, pyrimidinyl, pyrazinyl, pyranyl, furyl, benzofuryl, dibenzofuryl, thienyl, benzthienyl, indolyl, aza-indolyl, imidazolyl, oxadiazolyl and thiadiazolyl, which can be substituted by C$_{1-6}$ alkyl, halogen, C$_{1-6}$ alkoxy or nitro; or a heterocyclic group selected from the group consisting of: azetidinyl, pyrrolidyl, piperidyl, piperazinyl and morpholinyl groups; or represents an amino-protecting group, and L$^1$ represents a suitable leaving group; in the presence of a base.

13. A method for the treatment and/or prevention of disorders of the dopamine system, which method comprises administering to a patient in need of such treatment an effective amount of a compound as claimed in claim 1.

14. The process as claimed in claim 11 further comprising the step of removal of the amino-protecting group R$^{30}$ from the product of claim 11.

15. The process as claimed in claim 11 further comprising the step of removal of the amino-protecting group R$^{30}$ from the product of claim 11.

* * * * *